(12) United States Patent
Lai et al.

(10) Patent No.: US 7,183,437 B2
(45) Date of Patent: Feb. 27, 2007

(54) METHOD FOR PREPARING THREE TYPES OF BENZIDINE COMPOUNDS IN A SPECIFIC RATIO

(75) Inventors: Chun-Liang Lai, Chiayi Hsien (TW);
Kuan-Chieh Tseng, Pingtung (TW);
Chia-Hung Yeh, Pingtung Hsien (TW);
Ling Lu, Taoyuan Hsien (TW);
Charng-Lih Jeng, Tainan Hsien (TW);
Shyue-Ming Jang, Hsinchu (TW);
Bang-I Liou, Changhua Hsien (TW);
Chyuan Juang, Hsinchu (TW);
Yuan-Szu Chang, Tainan (TW);
Po-Han Huang, Tainan (TW)

(73) Assignees: Labeltek Inc. (TW); Taiwan Salt Industrial Corporation (TW)

( * ) Notice: Subject to any disclaimer, the term of this patent is extended or adjusted under 35 U.S.C. 154(b) by 191 days.

(21) Appl. No.: 10/681,163

(22) Filed: Oct. 9, 2003

(65) Prior Publication Data

US 2005/0080292 A1     Apr. 14, 2005

(51) Int. Cl.
*C07C 211/54* (2006.01)

(52) U.S. Cl. ...................................................... 564/309

(58) Field of Classification Search ................. 564/309
See application file for complete search history.

(56) References Cited

U.S. PATENT DOCUMENTS 4,764,625 A * 8/1988 Turner et al. ................ 548/442
5,929,281 A * 7/1999 Nishiyama et al. ......... 564/386

FOREIGN PATENT DOCUMENTS

JP     62-267749     * 11/1987

* cited by examiner

*Primary Examiner*—Joseph K. McKane
*Assistant Examiner*—Yong Chu
(74) *Attorney, Agent, or Firm*—Lowe Hauptman & Berner, LLP

(57) ABSTRACT

A method for preparing three types of benzidine compounds in a specific ratio, the method uses two types of diphenylamine compounds and one type of biphenyldihalide compound in a specific ratio as reactants to mix with an organic solvent and an additive to synthesize benzidine compounds in one step. The synthesized three types of benzidine compounds specially perform in a designated mixturing ratio having excellent photoelectric characteristics for a charge transporting layer in an organic photo-conductive drum.

9 Claims, 3 Drawing Sheets

METHOD FOR PREPARING THREE TYPES OF BENZIDINE COMPOUNDS IN A SPECIFIC RATIO

BACKGROUND OF THE INVENTION

1. Field of the Invention

The present invention relates to a method for preparing three types of benzidine compounds in a specific ratio, and more particularly to a method that prepares three desired types of benzidine compounds in specific chemical structures and in a desired ratio by using only one synthesizing step.

2. Description of Related Art

Benzidine compounds are important materials for photochemistry because of their electrical characteristics and are widely used in organic electroluminescence devices, light emitting diodes, xerographics, and charge transporting layers in printing machines.

A conventional method for preparing the benzidine compounds for a charge transporting layer is by using a metal catalyst such as copper, nickel, or palladium in cooperation with various ligands to couple halogenated benzene and diphenylamine into the benzidine compounds at high temperature. In order to make the charge transporting layer have excellent electrical characteristics, several desired kinds of benzidine compounds have to be mixed in a specific ratio to compose a composite material for the charge transporting layer. However, in the conventional method each kind of benzidine compound is prepared individually and then mixed with each other so that the conventional method is troublesome and time-wasting and has high manufacturing cost. Additionally, mixing the different kinds of benzidine compounds to compose a mixture of the benzidine compounds is hard to precisely control so that all batches are consistent, and so each batch of the mixture has differences in the quantity of added individual benzidine compounds. Therefore, the quality and the electrical characteristics of the mixture in different batches are irregular.

The present invention has arisen to provide a method for preparing three types of benzidine compounds in one step to overcome and obviate the drawbacks of the conventional method.

SUMMARY OF THE INVENTION

A first objective of the present invention is to provide a method for preparing three types of benzidine compounds in specific chemical structures and in specific equivalent ratio in only one step, whereby manufacturing processes of the charge transporting layer are simplified and manufacturing cost is reduced.

A second objective of the present invention is to provide a method for preparing three types of benzidine compounds in a specific ratio (compound 4:compound 5:compound 6=(86±3%):(13±2%):(0.2%~1.5%)).

Further benefits and advantages of the present invention will become apparent after a careful reading of the detailed description in company with drawings.

DETAILED DESCRIPTION OF THE PREFERRED EMBODIMENT

Figure 1:
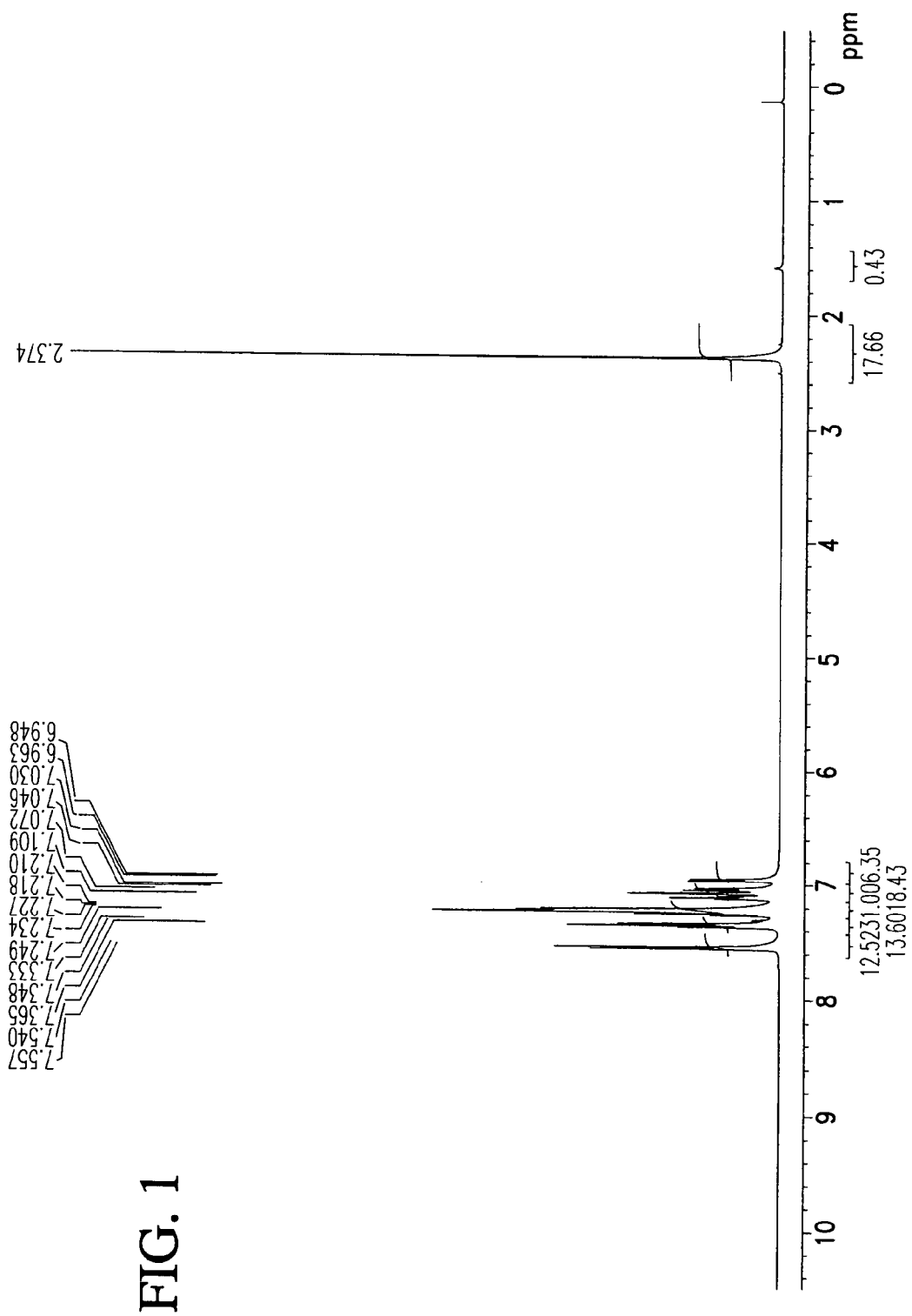
FIG. 1 is a NMR $^1$H spectrum of a mixture of three types of benzidine compounds prepared by a method in accordance with the present invention.

A method for preparing three types of benzidine compounds in a specific ratio in accordance with the present invention comprises the following chemical equation:

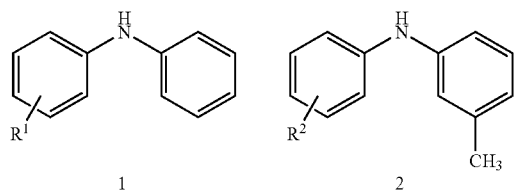
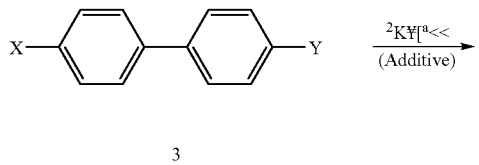

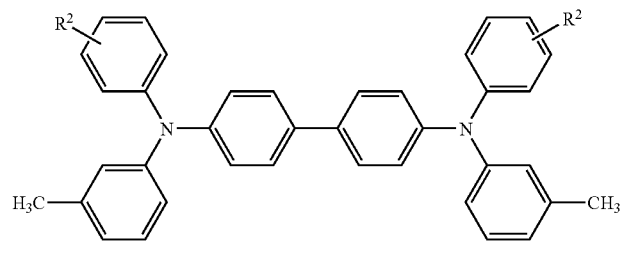

-continued

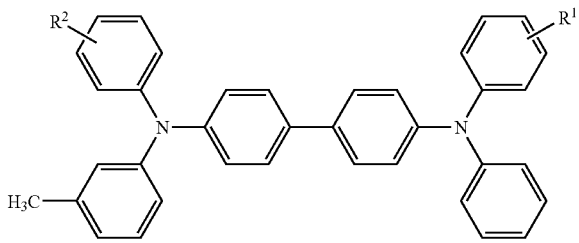

5

+

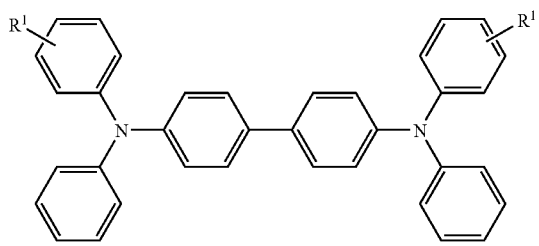

6 wherein $R^1$ and $R^2$ are selected from the group comprising a hydrogen, alkyl group containing 1–5 carbons, alkoxy group containing 1–5 carbons and benzene;

X is selected from the group comprising chlorine, bromine, and iodine;

Y is selected from the group comprising chlorine, bromine, and iodine.

In a preferred embodiment of the chemical reaction, $R^1$ is preferred to be hydrogen, $R^2$ is preferred to be hydrogen, X is preferred to be bromine, and Y is preferred to be bromine.

According to the foregoing chemical reaction, two types of aniline compounds (especially diphenylamine compounds as shown in compound 1 and compound 2 in the equation) and one type of halogenated biphenyl (especially biphenyldihalide as shown in compound 3 in the equation) are reactants and mixed together in a certain equivalent ratio, compound 1:compound 2: compound 3=(1):(1 1±0.3):(5±0.3), to synthesize products of benzidine compounds (compound 4, compound 5 and compound 6). Operational conditions of the synthesizing reaction are to add an organic solvent and an additive, apply heat up to 100~200° C. and then stir the mixture for 5 to 10 hours until the benzidine compounds are synthesized. The mixture is filtered at high temperature to obtain a filtering liquid. The synthesized benzidine compounds are still dissolved in the filtering liquid and re-crystallized to achieve the preparation of three types of benzidine compounds in high purity. The additive is a mixture of an organic metallic compound, an inorganic alkali and a ligand.

The solvent is selected from the group comprising: benzene, ether, alcohol, cyanoalkane and the mixture thereof. The organic metallic compound of the additive is selected from the group consisting of a palladium compound, a cuprous compound, a zinc compound and a nickel compound; and wherein the inorganic alkali is selected from the group consisting of sodium alkoxy, lithium alkoxy, sodium hydroxide, potassium hydroxide, potassium carbonate and potassium bicarbonate. The ligand of the additive is selected from the group comprising: dentate ether, 2,2'-bis(biphenylphosphino)-1,1'-binaphthyl compounds, alkyl phosphine, alkoxy phosphine, phenyl phosphine or pyridine.

After the reaction is completed, the crude benzidine compounds are obtained and further dissolved in a re-crystallizing solvent. The re-crystallizing solvent with benzidine compounds is heated up to a temperature range of 50–100° C. and filtered to remove any impurity from the re-crystallizing solvent. Then, benzidine compounds are extracted by a solid-liquid phase continuous extraction method and purified by a re-crystallizing process. The re-crystallizing solvent is selected from the group comprising: alkane solution, haloalkane solution, benzene solution, ether solution, ester solution and a mixture thereof. Lastly, a mixture of the white crystals the benzidine compounds (compounds 4, 5 and 6) with high purity is obtained. Wherein, the equivalent ratio of the three types of benzidine compounds in the mixture is a preferred mixture for a charge transporting layer in an organic photo-conductive drum. The equivalent ratio is of compound 4: compound 5:compound 6=(86±3%):(13±2%):(0.2~0.15%).

The following examples are shown to further illustrate details in the present invention.

EXAMPLE 1

A 5 L tri-neck round bottom flask (equipped with a mechanical stirrer, a thermal controller, and a condensing tube) was communicated with a nitrogen source and contained 500 g of dibromobiphenyl (1.6 moles), 620 g of 3-methyldiphenylamine (3.4 moles), 50 g of diphenylamine (0.3 mole), 168 g of potassium hydroxide (3 moles), 122 g of copper powder (1.76 moles) and 224 ml of Soltrol/70® (fatty mixture of $C_{13}$–$C_{15}$-purchased from Phillips Chemical Company). The mixture solution was heated to 165° C. for 7 hours and then 2.5 L Soltrol/70® (was added. The temperature of the mixture solution was lowered to 154° C. to filter inorganic solids and to obtain a filtering liquid. 2 L of methanol was added to the filtering liquid to accelerate crystallization of the benzidine compounds. Then, the filtering liquid was filtered again to obtain a yellow solid, which is a crude mixture of three types of benzidine compounds. Moreover, 2 L of methanol dissolved the crude mixture of benzidine compounds and filtered by 1.2 Kg of Woelm neutral alumina to obtain a light-yellow solid. Lastly, n-octane was used to dissolve the light-yellow solid and to re-crystallize the benzidine compounds in the form of white crystal. The white crystal weighed 500 g, has a melting point range of 168–170° C., and is a final mixture of the benzidine compounds having high purity.

EXAMPLE 2

A 5 L tri-neck round bottom flask (equipped with a mechanical stirrer, a thermal controller, and a condensing tube) was communicated with a nitrogen source and contained 500 g of dibromobiphenyl (1.6 moles), 620 g of 3-methyldiphenylamine (3.4 moles), 50 g of diphenylamine (0.3 mole), 24 L of toluene, 27 g of 1,10-phenanthroline (0.14 mole), 16 g of cuprous chloride (0.14 mole) and 168 g potassium hydroxide (3 moles). The mixture solution was stirred for 30 minutes and heated to 125° C. The mixture solution was further stirred to react for 6 hours and had added thereto 500 ml of toluene, 500 ml of deionized water and 400 g of acetic acid to neutralize the potassium hydroxide. The mixture solution was held at 70° C. and then poured into an extracting bottle to place for 10 minutes until layers of the mixture solution separated. An organic layer, i.e. a toluene solution, was removed from the mixture solution, washed with 1 L of deionized water twice and kept at 60° C. The toluene solution was filtered by 500 g of Woelm neutral alumina to obtain a filtering liquid. Then, the filtering liquid was dried to obtain 605 g of a crude mixture of benzidine compounds in the form of a white solid. Lastly, n-octane was used to dissolve the crude mixture and to re-crystallize the benzidine compounds in the form of pure white crystal. The pure white crystal weighed 500 g, has a melting point range of 169–170° C., and is a final mixture of the benzidine compounds having high purity.

EXAMPLE 3

A 5 L tri-neck round bottom flask (equipped with a mechanical stirrer, a thermal controller, a condensing tube, and a Dean-Stark device) was communicated with a nitrogen source and accommodated 500 g of dibromobiphenyl (1.6 moles), 620 g of 3-methyldiphenylamine (3.4 moles), 50 g of diphenylamine (0.3 mole), 2.5 L of xylene, 0.183 g of $Pd(OAc)_2$ (0.051 mole), 0.14 g of $P(t-Bu)_3$ (0.043 mole) and 350 g NaO-(t-Bu) (3.64 mole). The mixture solution was stirred for 30 minutes and heated to a reflux temperature of 125° C. The mixture solution was further stirred to react for 5 hours and had further added thereto 500 ml of o-xylene and 500 ml of deionized water. The mixture solution was held at 65° C. and poured into an extracting bottle to place for 10 minutes until layers of the mixture solution separated. An organic layer, i.e. an o-xylene solution, was removed from the mixture solution, washed with 1 L of deionized water twice and kept at 55° C. The o-xylene solution was filtered by 500 g of Woelm neutral alumina to obtain a filtering liquid. Then, the filtering liquid was dried to obtain 660 g of a crude mixture of benzidine compounds in the form of a white solid. Lastly, n-octane was used to dissolve the crude mixture and to re-crystallize the benzidine compounds in the form of pure white crystal. The pure white crystal weighed 580 g, has a melting point range of 168–170° C., and is a final mixture of the benzidine compounds having high purity.

EXAMPLE 4

A 5 L tri-neck round bottom flask (equipped with a mechanical stirrer, a thermal controller, a condensing tube, and a Dean-Stark device) was communicated with a nitrogen source and accommodated 500 g of dibromobiphenyl (1.6 moles), 620 g of 3-methyldiphenylamine (3.4 moles), 50 g of diphenylamine (0.3 mole), 2.4 L of toluene, 7.36 g of $Pd_2(dba)_3$ (0.008 mole) (prepared according to J. Org. Chem. 2000, 65, p. 5330) and 350 g NaO-(t-Bu) (3.64 mole). The mixture solution was stirred for 30 minutes and heated to a reflux temperature of 110° C. The mixture solution was further stirred to react for 5 hours and had further added thereto 500 ml of toluene and 500 ml of deionized water. The mixture solution was held at 55° C. and poured into an extracting bottle to place for 10 minutes until layers of the mixture solution separated. An organic layer, i.e. a toluene solution, was removed from the mixture solution, washed with 2 L of deionized water twice and kept at 55° C. The toluene solution was filtered by using 500 g of Woelm neutral alumina to obtain a filtering liquid. Then, the filtering liquid was dried to obtain 650 g of a crude mixture of benzidine compounds in the form of a yellow solid. Lastly, n-octane was used to dissolve the crude mixture and to re-crystallize the benzidine compounds in the form of pure white crystal. The pure white crystal weighed 550 g, has a melting point range of 169–170° C., and is a final mixture of the benzidine compounds having high purity.

EXAMPLE 5

A 5 L tri-neck round bottom flask (equipped with a mechanical stirrer, a thermal controller, and a condensing tube) was communicated with a nitrogen source and contained 500 g of dibromobiphenyl (1.6 moles), 620 g of 3-methyldiphenylamine (3.4 moles), 50 g of diphenylamine (0.3 mole), 2.4 L of xylene, 27 g of 1,10-phenanthroline (0.14 mole), 420 g of cuprous acetate-monohydrate (2.1 moles), 140 g of zinc (2.1 moles) and 552 g of calcium carbonate (4 moles). The mixture solution was stirred for 30 minutes and heated to 120° C. The mixture solution was further stirred to react for 10 hours and had further added thereto 500 ml of xylene, 500 ml of deionized water and 350 g of acetic acid to neutralize calcium carbonate. The mixture solution was held at 65° C. and poured into an extracting bottle to place for 10 minutes until layers of the mixture solution separated. An organic layer, i.e. a xylene solution, was removed from the mixture solution, washed with 1.5 L of deionized water twice and kept at 55° C. The xylene solution was filtered by 500 g of Woelm neutral alumina to obtain a filtering liquid. Then, 1 L of methanol was added to the filtering liquid to accelerate crystallization of benzidine compounds to obtain 595 g crude mixture of benzidine compounds in the form of a white solid. Lastly, n-octane was used to dissolve the crude mixture and to re-crystallize the benzidine compounds in the form of pure white crystal. The pure white crystal weighed 545 g, has a melting point range of 169–170° C., and is a final mixture of the benzidine compounds having high purity.

EXAMPLE 6

A 5 L tri-neck round bottom flask (equipped with a mechanical stirrer, a thermal controller, a condensing tube, and a Dean-Stark device) was communicated with a nitrogen source and accommodated 500 g of dibromobiphenyl (1.6 moles), 620 g of 3-methyldiphenylamine (3.4 moles), 50 g of diphenylamine (0.3 mole), 2.4 L of xylene, 27 g of 1,10-phenanthroline (0.14 mole), 16 g of cuprous chloride (0.14 mole) and 168 g of potassium hydroxide (3 moles). The mixture solution was stirred for 30 minutes and heated to a reflux temperature of 145° C. The mixture solution was further stirred to react for 7 hours and had further added thereto 1 L of o-xylene, 1 L of deionized water and 400 g of acetic acid to neutralize the potassium hydroxide. The mixture solution was held at 100° C. and poured into an extracting bottle to place for 10 minutes until layers of the mixture solution separated. An organic layer, i.e. an o-xylene solution, was removed from the mixture solution, washed with 1.5 L of deionized water twice and kept at 70° C. The o-xylene solution was filtered by 20 g of Alcoa-C neutral alumina to obtain a filtering liquid. Then, the filtering liquid was dried to obtain 615 g of a crude mixture of benzidine compounds in the form of a white solid. Lastly, n-octane was used to dissolve the crude mixture and to re-crystallize the benzidine compounds in the form of pure white crystal. The pure white crystal weighed 600 g, has a melting point range of 168–170° C., and is a final mixture of the benzidine compounds having high purity.

EXAMPLE 7

A 5 L tri-neck round bottom flask (equipped with a mechanical stirrer, a thermal controller, and a condensing tube) was communicated with a nitrogen source and contained 500 g of dibromobiphenyl (1.6 moles), 620 g of 3-methyldiphenylamine (3.4 moles), 50 g of diphenylamine (0.3 mole), 2.4 L of m-xylene (0.14 mole), 150 g of copper powder (2.4 moles), 168 g potassium hydroxide (3 moles) and 35 g of 18-crown-6-ether. The mixture solution was stirred for 30 minutes and heated to a reflux temperature of 139° C. The mixture solution was further stirred to react for 10 hours and had further added thereto 1 L of m-xylene, 1 L of deionized water and 400 g of acetic acid to neutralize the potassium hydroxide. The mixture solution was held at 65° C. and poured into an extracting bottle to place for 10 minutes until layers of the mixture solution separated. An organic layer, i.e. an m-xylene solution, was removed from the mixture solution, washed with 2 L of deionized water twice and kept at 55° C. The m-xylene solution was filtered by 600 g of Woelm neutral alumina to obtain a filtering liquid. Then, the filtering liquid was dried to obtain 620 g of a crude mixture of benzidine compounds in the form of a white solid. Lastly, n-octane was used to dissolve the crude mixture and to re-crystallize the benzidine compounds in the form of pure white crystal. The pure white crystal weighed 600 g, has a melting point range of 169–170° C., and is a final mixture of the benzidine compounds having high purity.

EXAMPLE 8

A 5 L tri-neck round bottom flask (equipped with a mechanical stirrer, a thermal controller, and a condensing tube) was communicated with a nitrogen source and accommodated 500 g of dibromobiphenyl (1.6 moles), 620 g of 3-methyldiphenylamine (3.4 moles), 50 g of diphenylamine (0.3 mole), 2 L of Soltrol®/170, 150 g of copper powder (2.4 moles) and 168 g potassium hydroxide (3 moles). The mixture solution was stirred for 30 minutes and heated to 190° C. The mixture solution was further stirred to react for 10 hours and had further added thereto 1 L of toluene, 1.5 L of deionized water and 400 g of acetic acid to neutralize the potassium hydroxide. The mixture solution was held at 65° C. and poured into an extracting bottle to place for 10 minutes until layers of the mixture solution separated. An organic layer, i.e. a toluene solution, was removed from the mixture solution, washed with 2 L of deionized water twice and kept at 55° C. The toluene solution was filtered by 500 g of Woelm neutral alumina to obtain a filtering liquid. Then, the filtering liquid was dried to obtain 630 g of a crude mixture of benzidine compounds in the form of a white solid. Lastly, n-octane was used to dissolve the crude mixture and to re-crystallize the benzidine compounds in the form of pure white crystal. The pure white crystal weighed 600 g, has a melting point range of 167–170° C., and is a final mixture of the benzidine compounds having high purity.

EXAMPLE 9

A 5 L tri-neck round bottom flask (equipped with a mechanical stirrer, a thermal controller, a condensing tube, and a Dean-Stark device) was communicated with a nitrogen source and accommodated 500 g of dibromobiphenyl (1.6 moles), 620 g of 3-methyldiphenylamine (3.4 moles), 50 g of diphenylamine (0.3 mole), 2.4 L of m-xylene, 27 g of 1,10-phenanthroline (0.14 mole), 16 g of cuprous chloride (0.14 mole) and 168 g potassium hydroxide (3 moles). The mixture solution was stirred for 30 minutes and heated to a reflux temperature of 139° C. The mixture solution was further stirred to react for 7 hours and had further added thereto 1 L of m-xylene, 1 L of deionized water and 400 g of acetic acid to neutralize the potassium hydroxide. The mixture solution was held at 65° C. and poured into an extracting bottle to place for 10 minutes until layers of the mixture solution separated. An organic layer, i.e. an m-xylene solution, was removed from the mixture solution, washed with 2 L of deionized water twice and kept at 55° C. The m-xylene solution was filtered by 600 g of Woelm neutral alumina to obtain a filtering liquid. Then, the filtering liquid was dried to obtain 610 g of a crude mixture of benzidine compounds in the form of a white solid. Lastly, n-octane was used to dissolve the crude mixture and to re-crystallize the benzidine compounds in the form of pure white crystal. The pure white crystal weighed 585 g, has a melting point range of 169–170° C., and is a final mixture of the benzidine compounds having high purity.

EXAMPLE 10

A 5 L tri-neck round bottom flask (equipped with a mechanical stirrer, a thermal controller, a condensing tube, and a Dean-Stark device) was communicated with a nitrogen source and accommodated 500 g of dibromobiphenyl (1.6 moles), 620 g of 3-methyldiphenylamine (3.4 moles), 50 g of diphenylamine (0.3 mole), 2.4 L of 10-crown-6-ether, 7.36 g of $Pd_2(dba)_3$ (0.008 mole) and 5.0 g 2,2'-bis(diphenylphosphino-1,1'-(binaphthyl) (0.008 mole). The mixture solution was stirred for 30 minutes and heated to a reflux temperature of 139° C. The mixture solution was further stirred to react for 6 hours and had further added thereto 1 L of m-xylene and 1 L of deionized water. The mixture solution was held at 65° C. and poured into an extracting bottle to place for 10 minutes until layers of the mixture solution separated. An organic layer, i.e. an m-xylene solution, was removed from the mixture solution, washed with 2 L of deionized water twice and kept at 55° C. The m-xylene solution was filtered by 600 g of Woelm neutral alumina to obtain a filtering liquid. Then, the filtering liquid was dried to obtain 630 g of a crude mixture of benzidine compounds in the form of a yellow solid. Lastly, n-octane was used to dissolve the crude mixture and to re-crystallize the benzidine compounds in the form of pure white crystal. The pure white crystal weighed 595 g, has a melting point range of 169–170° C., and is a final mixture of the benzidine compounds having high purity.

Figure 2:
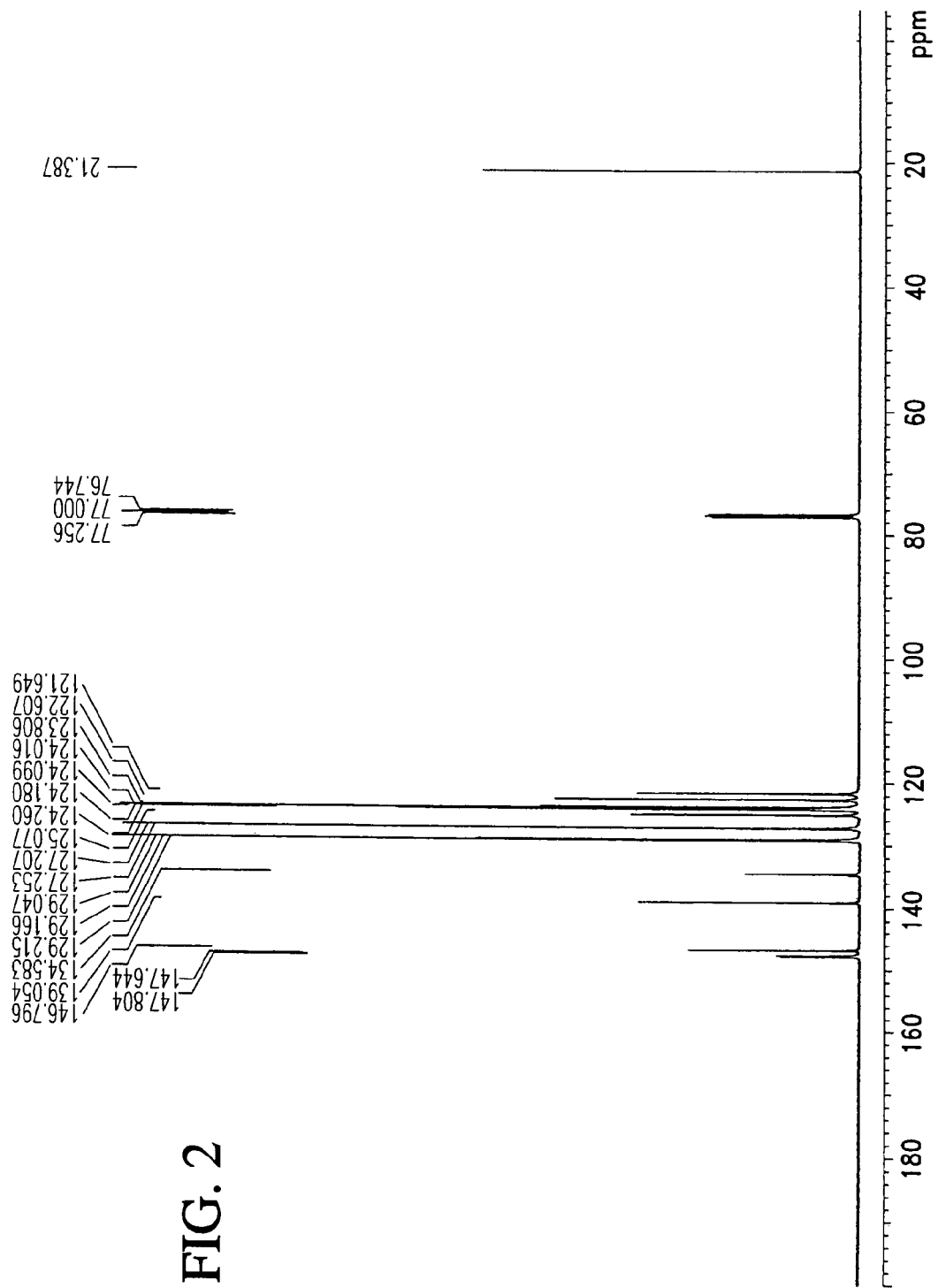
FIG. 2 is an NMR $^{13}$C spectrum of a mixture of three types of benzidine compounds prepared by a method in accordance with the present invention.
Figure 3:
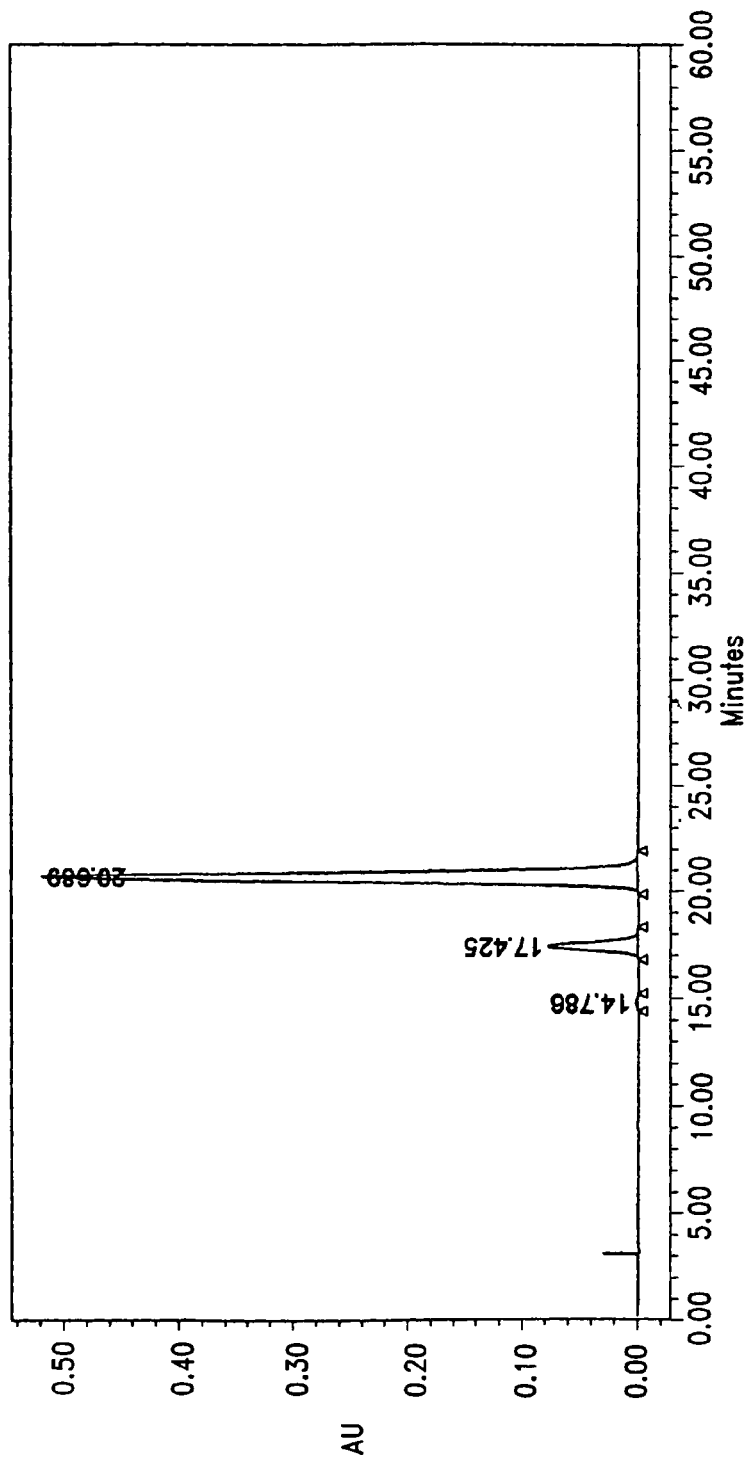
FIG. 3 is an HPLC chart of a mixture of three types of benzidine compounds prepared by a method in accordance with the present invention in comparison with a standard sample.

According to the foregoing examples, each example obtains a high-purity mixture of benzidine compounds that is tested for analysis by NMR and HPLC and shown in FIGS. 1 to 3. FIGS. 1 and 2 are spectrums respectively representing $^1$H standard test and $^{13}$C standard test to clarify the structure of the benzidine compounds according to compounds 4, 5 and 6. FIG. 3 is an HPLC testing result to show the ratio of benzidine compounds in the mixture. The ratio is specifically located within a standard sample purchased from Syntec Co., Germany, wherein the ratio is of compound 4: compound 5:compound 6=(86±3%):(13±2%): (0.2%~1.5%) as shown in FIG. 3. The standard sample shown in FIG. 3 was tested under the following operational conditions:

HPLC Type:
Pump: Waters 600
Detector: Waters 2996 Photodiode Array Detector
Autosampler: Waters 700 plus
Mobile Phase: 1% (v/v) Triethylamine, pH 7.5/Acetonitrile=5/95
Flow Rate: 1.0 mL/min
Column: Luna 5 μC18(2), 4.6*250-mm
Column Oven: 40 C
Injection Volume: 10 μL
Wavelength: 340 nm
RT.peak at 14.786 min indicates a retention time for compound 6(R1=H).
RT.peak at 17.425 min indicates a retention time for compound5(R1=H, R2=H).
RT.peak at 20.689 min indicates a retention time for compound 4(R2=H).
RT.retention time <Test for Photoelectric Characteristic>

To perform a test for a photoelectric characteristic, a charge generating layer has to be applied to an aluminum substrate and then a charge transporting layer containing the mixture of benzidine compounds is applied on the charge generating layer to achieve an organic photo-conductive drum.

The charge generating layer is composed of 50% of type IV polymorph of titanyloxyphthalocyamine and 50% of polyvinylbutyral.

The material of the charge transporting layer originally is a solution and comprises 40 wt % of the mixture of benzidine compounds prepared in examples 1–10, 60 wt % of polycarbonate-A (based on the weight of the charge transporting layer), and a composite solvent composed of dichloromethane and toluene.

1. Manufacturing Process

The charge generating layer was applied on the aluminum substrate and dried at 100° C. for 15 minutes to form a membrane of 0.3–0.5 μm.

Then, the material of the charge transporting layer was applied on the charge generating layer and dried at 100° C. for 60 minutes to form a membrane of 24 μm, i.e. the charge transporting layer.

Whereby, an organic photo-conductive drum was achieved.

2. Photoelectric Characteristic

The achieved organic photo-conductive drum was tested by using PDT-2000LA instrument (QEA Inc. SN:02021501070217). Multiple photoelectric characteristics were listed in the following table:

| Examples | $V_0$ | $V_r$ | $E_{1/2}$ | $D_kD_{ec}$ (%) |
| --- | --- | --- | --- | --- |
| HP-4100 | 688.22 | 48.41 | 0.082 | 97.0 |
| 1 | 687.18 | 32.26 | 0.090 | 95.9 |
| 2 | 682.58 | 32.01 | 0.086 | 95.5 |
| 3 | 691.54 | 29.16 | 0.081 | 95.6 |
| 4 | 675.35 | 32.60 | 0.083 | 96.0 |
| 5 | 708.20 | 37.9 | 0.083 | 96.2 |
| 6 | 706.81 | 39.67 | 0.083 | 96.3 |
| 7 | 704.56 | 35.36 | 0.091 | 97.6 |
| 8 | 705.02 | 29.26 | 0.087 | 97.2 |
| 9 | 678.17 | 27.52 | 0.100 | 96.2 |
| 10 | 679.27 | 29.14 | 0.095 | 95.6 |

$V_0$ applying potential
$V_r$ residual potential tested at a moment of six times of half-time
$E_{1/2}$ sensitivity energy for decaying half-quantity of light
$D_kD_{ec}$ dark decay Embodiments of the organic photo-conductive drum using the benzidine compounds in the present invention were tested to compare with the organic photo-conductive drum of HP company. All embodiments conformed with the following photoelectric requirements:

$V_0$(applying potential).670 volt
Vr(residual potential).60 volt
E1/2(sensitivity.0.1±0.02 μj/cm2
$D_kD_{ec}$(dark decay).95%

According to the table, the embodiment applied with the benzidine compounds in the present invention has lower residual potential than HP's organic photo-conductive drum.

The present invention provides a method for preparing benzidine compounds, that manufactures three specific types of benzidine compounds in a specific ration in one step by mixing two diphenylamine compounds and one biphenyldihalide compound in a proper equivalent ration and reacting under proper operational conditions. Therefore, the final mixture of the benzidine compounds enables to be directly applied on the organic photo-conductive drum without any extra treatment yet still has excellent photoelectric characteristics. Therefore, the method for preparing three types of benzidine compounds in a specific ratio in the present invention is easier than the conventionally troublesome method that prepares each benzidine compound individually, and so operation time and manufacturing cost are diminished.

Although the invention has been explained in relation to its preferred embodiment, many other possible modifications and variations can be made without departing from the spirit and scope of the invention as hereinafter claimed.

What is claimed is:

1. A method for preparing three types of benzidine compounds:

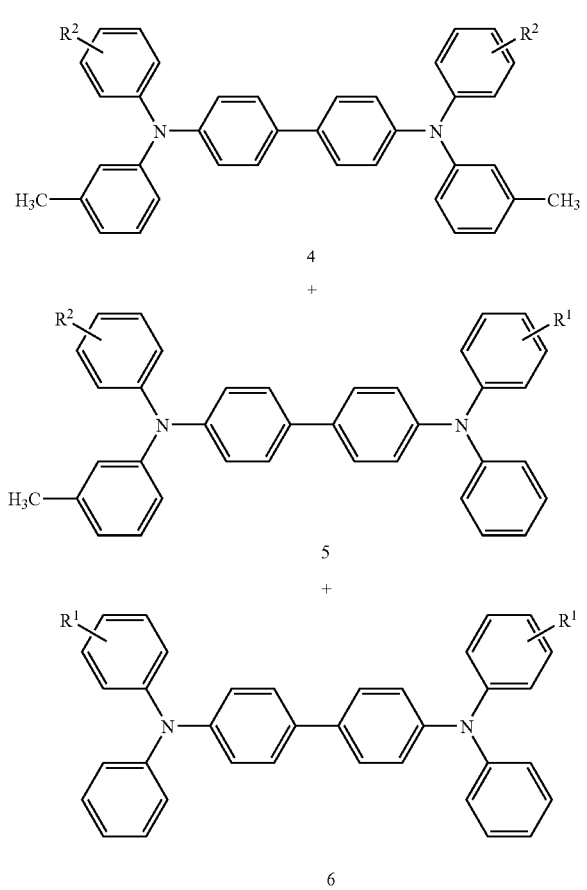

in an equivalent ratio of compound 4: compound 5: compound 6 of (86″3%):(13″2%):(0.2–1.5%), the method comprising reacting compound 1, compound 2 and compound 3:

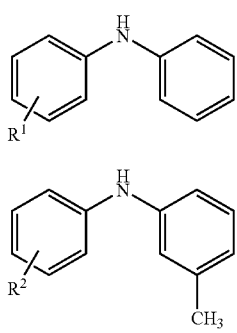

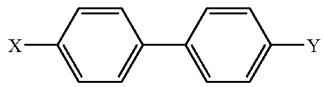

where compound 1 is a first diphenylamine compound, compound 2 is a second diphenylamine compound, and compound 3 is a biphenyldihalide compound, in the presence of an additive at 100–200° C., to produce a mixture of compound 4, compound 5 and compound 6 in said equivalent ratio, wherein the additive comprises an organic metallic compound, an inorganic alkali, and a ligand wherein compound 1, compound 2 and compound 3 are reacted in an equivalent ratio of compound 1: compound 2: compound 3 of (1):(11″0.3):(5″0.3), and the reacting takes place in a solvent selected from the group consisting of benzene, ether, ethanol, a cyanoalkane and mixtures thereof; and $R^1$ and $R^2$ are selected from the group consisting of hydrogen, an alkyl group containing 1–5 carbons, an alkoxy group containing 1–5 carbons and benzene;

X is selected from the group consisting of chlorine, bromine, and iodine; and

Y is selected from the group consisting of chlorine, bromine, and iodine.

2. The method as claimed in claim 1, wherein the organic metallic compound is selected from the group consisting of a palladium compound, a cuprous compound, a zinc compound, and a nickel compound.

3. The method as claimed in claim 1, wherein the inorganic alkali is selected from the group consisting of sodium alkoxy, lithium alkoxy, sodium hydroxide, potassium hydroxide, potassium carbonate and potassium bicarbonate.

4. The method as claimed in claim 1, wherein the ligand is selected from the group consisting of dentate ether, 2,2'-bis(biphenylphosphino)-1,1'-binaphthyl compounds, alkyl phosphine, alkoxy phosphine, phenylphosphine and pyridine.

5. The method as claimed in claim 1, additionally comprising extracting, filtering, and then purifying the mixture with a re-crystallizing solvent.

6. The method as claimed in claim 5, wherein the mixture is extracted by a liquid-solid phase serial extracting method.

7. The method as claimed in claim 5, wherein the mixture is filtered at a temperature range of 50–100° C.

8. The method as claimed in claim 5, wherein the mixture is re-crystallized in a solvent selected from the group consisting of an alkane, a haloalkane, benzene, an ether, an ester, and mixtures thereof.

9. The method as claimed in claim 1, wherein $R^1$ is hydrogen; $R^2$ is hydrogen; X is bromine; and Y is bromine.

* * * * *